United States Patent [19]

Sovak et al.

[11] Patent Number: 5,035,877

[45] Date of Patent: Jul. 30, 1991

[54] NON-IONIC CONTRAST MEDIA FROM IONIC CONTRAST MEDIA

[75] Inventors: Milos Sovak, Rancho Santa Fe; Ramachandran Ranganathan, San Diego, both of Calif.

[73] Assignee: Cook Imaging Corporation, Bloomington, Ind.

[21] Appl. No.: 582,791

[22] Filed: Sep. 14, 1990

Related U.S. Application Data

[63] Continuation of Ser. No. 402,965, Sep. 5, 1989, abandoned, which is a continuation of Ser. No. 110,092, Oct. 13, 1987, abandoned, which is a continuation of Ser. No. 764,274, Aug. 9, 1985, abandoned.

[51] Int. Cl.$^5$ .................. C07C 237/46; A61K 31/165; A61K 49/04
[52] U.S. Cl. ......................................... 424/5; 564/153
[58] Field of Search ............................. 564/153; 424/5

[56] References Cited

U.S. PATENT DOCUMENTS

| | | | |
|---|---|---|---|
| 3,622,616 | 11/1971 | Guerbet et al. | 424/5 X |
| 3,701,771 | 10/1972 | Almen et al. | 424/5 X |
| 3,702,866 | 11/1972 | Salvesen et al. | 424/5 X |
| 3,867,431 | 2/1975 | Felder et al. | 424/5 X |
| 4,001,323 | 1/1977 | Felder et al. | 424/5 X |
| 4,021,481 | 5/1977 | Almen et al. | 424/5 X |
| 4,160,015 | 7/1979 | Wiegert | 424/5 |
| 4,250,113 | 2/1981 | Nordal et al. | 424/5 X |
| 4,341,756 | 7/1982 | Sovak et al. | 424/5 |
| 4,364,921 | 12/1982 | Speck et al. | 424/5 |
| 4,396,597 | 8/1983 | Rakli et al. | 424/5 |
| 4,396,598 | 8/1983 | Lin | 424/5 |
| 4,547,357 | 10/1985 | Pfeiffer et al. | 424/5 |

FOREIGN PATENT DOCUMENTS 108008 7/1967 Denmark ............................. 562/455

OTHER PUBLICATIONS

Havaaveldsen et al., Acta Pharm. Suec. 20, 232, (1983), pp. 219-232.

*Primary Examiner*—Carolyn Elmore
*Attorney, Agent, or Firm*—Woodard, Emhardt, Naughton, Moriarty & McNett

[57] ABSTRACT

Novel non-ionic contrast media are efficiently prepared from generally available ionic contrast media. Particularly, polyhdroxyhalohydrocarbons are employed with a triiodo-substituted acylamido benzoic acids in aqueous weakly basic media to selectively substitute the amido nitrogen, followed by activation of the carboxyl group for amide formation.

1 Claim, No Drawings

NON-IONIC CONTRAST MEDIA FROM IONIC CONTRAST MEDIA

This application is a continuation of application Ser. No. 402,965, filed Sep. 5, 1989, which is a continuation of application Ser. No. 110,092, filed Oct. 13, 1987, which is a continuation of Ser. No. 764,274, filed Aug. 9, 1985, now all abandoned.

BACKGROUND OF THE INVENTION

1. Field of the Invention

Medical imaging with X-rays depends to a great extent upon radiographic contrast media (CM). An ideal CM, designed to mix with the body fluids, should be economically feasible, chemically stable, high water soluble, readily injectable, and biologically inert. CM of prior art, based on salts of derivatized triiodinated benzene moieties and meet the first four criteria, but they induce adverse clinical effects. Such toxicity extends from their ionicity, solution hyperosmolality vis-a-vis the body fluids, and chemotoxicity reflecting their relatively high hydrophobicity.

Non-ionic, less hyperosmolal, less hydrophobic but more costly compounds exist, of which Metrizamide is used clinically in the United States. Metrizamide suffers from hydrolytic instability, and thus must be dispensed lyophilized and reconstituted prior to use. Solutions of some other non-ionic, stable CM have, however, high osmolality and thus elicit pain when injected into the arteries. Other compounds are, at elevated concentrations, not persistently water soluble. All current non-ionic CM, while less toxic than the prior art, are much more costly.

Consequently despite the large number of compound which have been prepared, there is substantial interest in producing improved non-ionic CM improved both pharmacologically and economically. To this end, in developing novel synthetic strategies, it is essential once the ring has been iodinated that subsequent steps are few and have high yields. Furthermore, the iodinated substrate, as well as the reactants that are employed for additional functionalization, should be inexpensive.

BRIEF DESCRIPTION OF THE RELEVANT LITERATURE

There is an extensive patent literature concerned with non-ionic contrast media and their method of preparation. See particularly, U.S. Pat. Nos. 4,364,921; 4,341,756; 4,250,113; 4,021,481; 4,001,323; 3,702,866; 3,701,771; and 3,622,616. See also, "Radiocontrast Agents", Volume 73 of the Handbook of Experimental Pharmacology, Springer, New York, 1985, which provides a comprehensive review of the field as of the time of publication.

SUMMARY OF THE INVENTION

Non-ionic contrast media are prepared by selective and efficient polyhydroxyalkylation of the nitrogen of an acylamido substituted triiodobenzoic acid with a polyhydroxyalkyl halide in an aqueous medium under weakly basic conditions. The polyhydroxyalkylated acylamidobenzoic acid may then be activated for formation of functionalized benzamides. The methodology provides for an economic and efficient synthetic approach to known and novel non-ionic contrast media.

DESCRIPTION OF THE SPECIFIC EMBODIMENTS

Novel methods are provided for producing non-ionic contrast media employing triiodo persubstituted acylamidobenzoic acid as starting materials, preferably available ionic contrast media. The method involves selective and efficient alkylation of the nitrogen of the acylamido group with a halohydrin under weakly basic conditions in aqueous medium, followed by protection of hydroxyl groups, activation of the benzoic acid group and amidation of the activated benzoic acid group. The protective groups will then be removed to provide the final product. The synthetic strategy employs readily available reagents, which are for the most part inexpensive, and results in high yields of readily purifiable intermediates and final product.

The starting materials will be 5-acylamido substituted triiodobenzoic acids, where the 3-position will be substituted with a substituted amino group or a carboxamido group. The starting materials will normally have at least about 10 carbon atoms, and usually from 0 to 2, more usually from 0 to 1, hydroxyl group. The product will usually have less than 20 carbon atoms, more usually fewer than about 18 carbon atoms, and will have at least three nitrogen atoms, of which at least one will be substituted to an annular carbon atom while one or both of the nitrogen atoms may be amido. Acyl groups bound to nitrogen will generally have from 1 to 4 carbon atoms, usually from 2 to 3 carbon atoms, and from 0 to 3 oxy substituents, more usually from 0 to 2 oxy substituents. Alkyl substituents will be generally of from 1 to 3 carbon atoms, more usually of from 1 to 2 carbon atoms, and having from 0 to 3 hydroxyl groups, more usually from 0 to 2 hydroxyl groups.

The following flowchart indicates the synthetic strategy. TIB intends triiodobenzene, where the vertical line indicates the groups associated with the horizontal lines are bound at the 1, 3, and 5 positions, respectively. The numbers over the arrows indicate the reaction, with the legend indicating the reagents and conditions for the reaction.

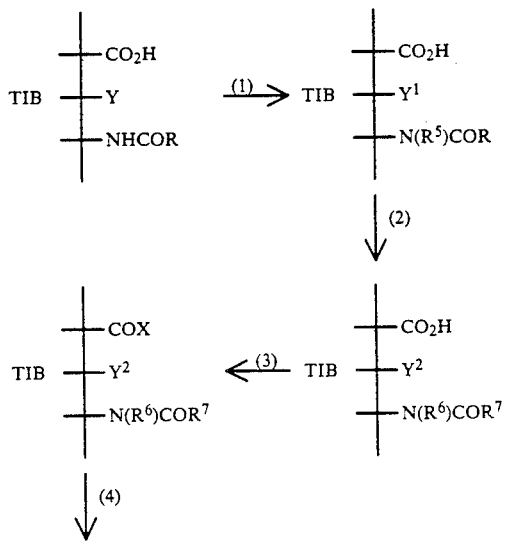

-continued

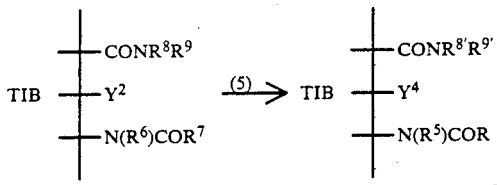

(1) halohydrin of 2 to 5 carbon atoms and 1 to 4 oxy groups; aqueous base, pH 9-13, 60-100° C., 0.5-6 hr.
(2) AcZ, Z = chloro or AcO, where Ac is an acyl group of from 2 to 3 carbon atoms; tert.-amine, 50-80° C., 1-6 hr.
(3) G—Cl (G-inorganic or organic acyl group); 50-80° C.; 0.25-3 hr.
(4) HNR$^8$R$^9$; tert.-amine, 35-75° C.
(5) (a) OH$^-$; (b) neutralization, optionally acidification when acetonides are present.

The symbols are defined as follows:
TIB = 2,4,6-triiodobenzene;
Y = NR$^1$R$^2$ or or CONR$^3$R$^4$ or CH$_2$NR$^2$COR$^3$;
R = an aliphatic group Of from 1 to 3, usually 2 to 3 carbon atoms, having from 0 to 2, usually 0 to 1 oxy groups;
R$^1$ = hydrogen, an aliphatic group of from 1 to 3, usually 1 to 2 carbon atoms, having from 0 to 2, usually 0 to 1 oxy groups, an aliphatic acyl group of from 1 to 3, usually 1 to 2 carbon atoms, and from 0 to 2, usually 0 to 1 oxy groups;
R$^2$ = the same or different from R$^1$, usually R$^2$ will be hydrogen or an aliphatic group; at least one of R$^1$ and R$^2$ being other than hydrogen;
R$^3$ = hydrogen or an aliphatic group of from 1 to 3, usually 1 to 2 carbon atoms, having from 0 to 2, usually 0 to 1 oxy groups;
R$^4$ = the same or different from R$^3$, usually hydrogen;
R$^5$ = mono- or polyoxyalkyl from 2 to 5, usually 2 to 4, preferable 3 to 4 carbon atoms, having from 1 to 4, usually 1 to 2 oxy groups;
Y$^1$ = NR$^1$R$^{2'}$ or CONR$^3$R$^4$;
R$^{2'}$ = the same as R$^2$ with the proviso that when R$^2$ is hydrogen and Rhu 1 is acyl or an aliphatic group, then R$^{2'}$ includes mono- or polyoxyalkyl of from 2 to 5, usually 2 to 4, preferably 3 to 4 carbon atoms having from 1 to 3, usually 1 to 2 oxy groups;
R$^6$ = the same as R$^5$, except all hydroxyl groups of R$^5$ are acyloxy groups, where Ac is bonded to the hydroxyl oxygen;
R$^7$ = the same as R, except all hydroxyl groups of R$^5$ are acyloxy groups, where Ac is bonded to the hydroxyl oxygen;
Y$^2$ = the same as Y$^1$, except all hydroxyl groups of Y$^1$ are acyloxy groups, where Ac is bonded to the hydroxyl oxygen;
R$^8$ and R$^9$ = the same or different and are hydrogen or alkyl of from 1 to 4 carbon atoms having 0 to 3, usually 1 to 3 oxy groups, the total number of carbon atoms being not greater than about 6, usually not greater than about 4;
R$^8$ and R$^{9'}$ = the same as R$^8$ and R$^9$ except are without alkoxy groups;
Ac = an aliphatic acyl group of from 2 to 3 carbon atoms, particularly acetyl;
X = halo or 2-oxypyridile, N-oxysuccinimidile or iso-ureido;
Y$^4$ = Y$^1$ or Y.
Each of the stages will now be considered in detail. The starting compound will be an acylamido, triiodo substituted benzoic acid, where the other substituent is a carboxamido group or an acylamido group. Desirably, the starting materials may be ionic contrast media, so as to provide a commercially available and inexpensive starting material. Such compounds include derivatives of triiodo-3,5-diaminobenzoic acid, diatrizoate, 3,5-diacetamido-2,4,6-triiodobenzoic acid; and metrizoate, the N-mono-methyl derivative of diatrizoate, and derivatives of 5-aminoisophthalic acid, iothalamate, 5-acetamido-2,4,6-triiodo-N-methylisophthalamic acid; and ioxithalamic acid, 5-acetamido-2,4,6-triiodo-N-(2-hydroxyethyl)-isophthalamic acid). While generally available ionic contrast media are preferred as starting materials, any of the triiodobenzoic acid derivatives substituted at the 3 and 5 positions with amino and carboxy groups having various useful substituents may be employed.

The method will now be described in further detail. The first step is the reaction of the acylamido substituted triiodobenzoic acid with a halohydrin of from 2 to 5 carbon atoms, usually 3 to 4 carbon atoms, particularly a chlorohydrin, preferably where the chloro group is a primary or secondary chloro group, there being from 1 to 4 oxy groups, at least one of the oxy groups being hydroxy to provide a vicinal halohydrin. The reaction will be carried out in aqueous base, normally a basic solution of at least pH 9, generally from about pH 9 to pH 14, more usually from about pH 9.5 to pH 13.5. Stoichiometric amounts of the halohydrin may be employed, usually a small excess, not exceeding two molar excess, usually not exceeding one molar excess. The pH is maintained during the course of the reaction. Temperatures will normally be at least about 45° C. and not exceeding about 100° C., preferably between 45° C. to 95° C. The reaction is carried out until completion, which can be monitored by TLC or HPLC. Generally, fewer than 2hr are required, frequently fewer than 1hr. An aqueous medium is employed which may or may not have cosolvents. Since an aqueous medium suffices, cosolvents will usually not be employed.

At completion of the reaction, the product need not be isolated and purified, rather the medium may be neutralized to a mildly acidic pH, usually from about pH 4 to pH 6 and the solvents removed, e.g., azeotroped with an appropriate cosolvent, e.g., pyridine or toluene. The residue may then be used directly in the next step.

The next stage is the protection stage, where hydroxyl groups will be reacted with an appropriate reagent which is stable under the reaction conditions of the next successive steps. Since the next successive steps will involve acidic reagents, the protective groups will be those which will be able to survive the subsequent reactions. The reagents employed for the protection will of course be reactive, so as to react with the hydroxyl groups and any available amino group, will not interfere with the reactions of the carboxyl group to form an amide, and will allow for easy recovery of the product free of the protective groups. Furthermore, since economics are important to the synthetic strategy, normally inexpensive groups will be employed. However, other groups could be used less efficiently and less economically.

Of particular interest is the use of acylhalides and acyl anhydrides of from 1 to 3, preferably 2 carbon atoms, particularly acetic anhydride. With acetic anhydride, the anhydride may serve as the solvent and will therefore be in substantial excess, the particular amount will usually be at least about 2- to 3-fold molar excess. With other agents, they may either be used as the solvent, when appropriate, or an inert solvent may be employed such as acetonitrile, ethyl acetate or dichloromethane. In addition to the anhydride, an activating catalyst will be employed, particularly a tertiary amino compound, more particularly pyridine. The temperatures will be higher than room temperature, generally in the range of about 40–60° C., and the reaction will usually require about 1–6hr, depending upon the particular reagent and the size of the reaction batch. The course of the reaction may be followed by TLC.

Workup will normally involve removal of the solvents by evaporation and azeotroping, as appropriate. The residue may then be dissolved in water and the aqueous layer extracted with a water immiscible polar organic solvent, e.g., an ester, convenient ethyl acetate, in admixture with a nonpolar solvent, such as toluene. The aqueous layer may then be acidified to precipitate the hydroxy protected benzoic acid and the precipitate dissolved into an organic extractant, conveniently the same organic extractant, and the organic extracts combined and the product isolated in conventional ways.

The hydroxy protected benzoic acid compound is then activated, so as to be reactive with an aliphatic amine. A variety of ways are available for activation of the carboxy group. O-acylureas can be formed, by employing carbodiimides, or the like. Active esters may be prepared, such as N-oxysuccinimide, 2-acyloxypyridyl, nitrophenyl, chlorophenyl, or the like. While the particular manner in which the carboxyl group is activated is not critical to this invention, the preferred method is to prepare the acyl chloride employing an inorganic or organic acid halide, particularly an inorganic halide, such as thionyl chloride, sulfuryl chloride, phosphorus pentachloride, or the like. Of particular interest is the use of thionyl chloride, where the thionyl chloride may be used as the solvent and be present in excess, usually at least about 1 to 4 molar excess and the reactant dissolved in the thionyl chloride. Alternatively, the compound may be dissolved in an inert solvent such as dichloromethane or ethyl acetate and thionyl chloride employed in a small excess, usually 2 to 4 molar excess. The mixture will be heated at an elevated temperature, generally from about 50–75° C. for a sufficient time for the reaction to go to completion, generally from about 0.25 to 3hr. The reaction may be monitored by TLC. The thionyl chloride and other incipient solvents may then be removed by evaporation and as appropriate azeotroping the residue to remove any residual thionyl chloride and the resulting product dissolved in an inert polar organic solvent, e.g., an ester, followed by washing with bicarbonate and drying the organic layer.

The activated carboxyl, particularly the acyl halide, may then be combined in an inert organic polar solvent, conveniently an ether or an amide, more conveniently dioxane or dimethylacetamide with an acid neutralizing compound, conveniently a tertiary amino compound. The amino compound may be ammonia or alkylamino of from 1 to 4 carbon atoms, having from 0 to 3, usually from 0 to 2 hydroxy groups, which may be protected or unprotected, when protected, as ethers, particularly acetals or ketals, more particularly acetonide. The reaction is carried out under mild conditions at room temperature or at an elevated temperature, generally from about 40–70° C. until completion, which will usually require about 0.5hr and fewer than 12hr, usually fewer than 9hr.

The workup follows prior workups, in that the solvents are evaporated, the product dissolved in an appropriate polar organic solvent and washed with water with or without added sodium chloride. The organic layers may then be dried and the solvent removed by evaporation. In each instance, the isolation steps are conventional.

The hydroxyl groups are then deprotected employing a basic medium, usually a basic alkanolic medium, particularly methanol, the pH being at least about 10, and hydroxyl concentration being less than 1 normal. The reaction may be carried out under mild conditions, usually ambient temperatures being satisfactory, the reaction usually being complete in less than about 2hr. Volatile materials may then be removed by evaporation and the residue neutralized with aqueous acid, also under ambient conditions. Conveniently, a pH of 1 to 2 may be employed to remove acetonide functions when they are present. Desirably, the product may be further purified by desalting with an appropriate ion exchange resin.

A wide variety of compounds may be made in accordance with the subject invention. Of particular interest are the novel compounds 5-(N-2,3-dihydroxypropylacetamido)-2,4,6-triiodo-N-(2,3-dihydroxypropyl)-N'-(2-hydroxyethyl)-isophthalamide (compound VIII in the Experimental Section) and 5-(N-2,3-dihydroxypropylacetamido)-2,4,6-triiodo-N-methyl-N'-(1,3,4-trihydroxy threo-but-2-yl)-isophthalamide compound XVIII in the Experimental Section).

These particular compounds are found to have excellent properties as to toxicity, water solubility, osmolality, stability, viscosity and the like, factors predominantly important in angio and urography.

The subject compounds may be used as contrast media for angiography, urography and specification of body cavities.

These novel compounds are suitable as opacifying compounds in all fields of application of water-soluble non-ionic X-ray contrast media, especially for intravasal, subarachnoid and various local applications for which presently available non-ionic contrast media are employed.

The subject compounds can be formulated in accordance with conventional techniques, using pharmaceutically acceptable organic or inorganic carrier substances, suitable for parenteral or enteral application for administration to a patient. Conventional pharmaceutically acceptable carriers include but are not limited to water, saline solution, alcohols, vegetable oils, polyethylene glycols, gelatin, lactose, amylose, magnesium stearate, paraffin oils, fatty acid mono- and diglycerides, pentaerythritol fatty acid esters, hydroxymethylcellulose, polyvinyl pyrrolidone, talc, etc.

Other additives which are conventional in galenic pharmacy include stabilizers, such as sodium edetate, calcium disodium edetate, physiologically compatible buffers, sodium chloride, etc.

For parenteral application, useful solutions include the oily or aqueous solutions, as well as suspensions or emulsions. Ampules are convenient for unit dosages.

For enteral application, particularly suitable are tablets or dragees, having talc and/or a carbohydrate carrier or binder or the like, the carrier preferably being lactose and/or cornstarch and/or potato starch. A syrup or similar sweetener may be employed. Sustained release compositions can also be formulated, where the active compound is protected with differentially degradable coatings, e.g., by microencapsulation, multiple coatings, etc.

For intravenous administration, the subject compounds will normally be used in aqueous medium, where the concentration will be about 15 to 80 vol. percent, the active agent per unit dosage being about 1 to 80g, usually 2 to 70g.

Preferred concentrations in aqueous media will generally be from about 50–400mg I/ml, preferably about 100–400mg I/ml, with dosages running from about 2 to 500ml.

The following examples are offered by way of illustration and not by way of limitation:

EXPERIMENTAL

Example 1. Alkylation of ioxithalamic acid

5-Acetamido-2,4,6-triiodo-N-(2-hydroxyethyl)isophthalamic acid (I) into:
5-(N-2,3-Dihydroxypropylacetamido)-2,4,6-triiodo-N-(2-hydroxyethyl)-isophthalamic acid (II)

To ioxithalamic acid (161g, 0.25 moles) was added 1N sodium hydroxide (250ml) and the pH adjusted with 5N NaOH to 10.5–10.6 at 85–90° C. 1-Chloro2,3-propanediol (30.41g, 0.275 moles) was added and the pH readjusted to 10.5–10.6 with 5N NaOH, followed by further additions at 1hr (2.76, 0.025 moles) and at 2hr (2.76g, 0.025 moles). The reaction was complete at 2.5hr by TLC.

Glacial acetic acid was added to pH 5, solvents were evaporated and the residue azeotroped with toluene (150ml) to obtain 294g of a mixture which was used without product isolation into the next step.

Example 2. Acetylation of N-alkylated ioxithalamic acid 5-(N-2,3-Dihydroxypropylacetamido)-2,4,6-triiodo-N-(2-hydroxyethyl)-isophthalamic acid (II) into:
5-(N-2,3-Diacetoxypropylacetamido)-2,4,6-triiodo-N(2-acetoxyethyl)-isophthalamic acid (III)

The crude mixture (290g) from step one, containing the title compound (250mMoles), was suspended in acetic anhydride (500ml) and pyridine (19.76g, 250mMoles) and mechanically stirred at 65° C. By TLC, the acetylation was complete after 3hr.

The acetic anhydride and pyridine were evaporated, and the residue azeotroped with toluene (100ml×2). The residue was dissolved in saturated aqueous sodium bicarbonate (500ml) and ethyl acetate (200ml). The layers were separated, and the bicarbonate layer re-extracted with ethyl acetate (200ml×2). The aqueous layer was acidified with concentrated hydrochloric acid to pH 0–1 to obtain a white precipitate which was extracted with ethyl acetate (3×200ml). The organic extracts were combined and washed with brine (100ml), and dried over MgSO4. Removal of the solvent gave 206g of the product (III) as a white foam (97% yield).

Example 3. Acyl-chloride formation of N-alkylated, acetylated ioxithalamic acid 5-(N-2,3-Diacetoxypropylacetamido)-2,4,6-triiodo-N(2-acetoxyethyl)-isophthalamic acid (III) into:
5-(N-2,3-Diacetoxypropylacetamido)-2,4,6-triiodo-N(2-acetoxyethyl)-isophthalamic acid chloride (IV) 15 The title compound (III) (205g, 243mMoles) was dissolved in thionyl chloride (400ml), and the reaction mixture heated at 60–65° C. for 1hr to completion (by TLC). The thionyl chloride was evaporated on a rotary evaporator, the residue azeotroped with ethyl acetate (250ml×2), the product dissolved in ethyl acetate (400ml), extracted with aqueous saturated bicarbonate (150ml×2) and dried over MgSO4 to give 202g of an off-white foam (96% yield).

Example 4. Amidation of alkylated, acetylated ioxithalamic acid chloride with trans-dioxepane (protected amino-threitol)

5-(N-2,3-Diacetoxypropylacetamido)-2,4,6-triiodo-N(2-acetoxyethyl)-isophthalamic acid chloride (IV) into:
5-(N-2,3-Diacetoxypropylacetamido)-2,4,6-triiodo-N2-acetoxyethyl)-N'-(trans-2,2-dimethyl-6-hydroxy-1,3-dioxepan-5-yl)-isophthalamide (V)

The title compound (86.25g, 100mMoles) was dissolved in dimethylacetamide (200ml) to which was added ethylamine (13.9ml, 100mMoles) and trans-5-amino-2,2-dimethyl-6-hydroxy-1,3-dioxepane (19.3g, 120mMoles). The reaction mixture was stirred at room temperature for 8hr to completion (by TLC). The solvent was evaporated in vacuo and the residue dissolved in ethyl acetate (200ml). The solution was washed with water (3×50ml) and brine (2×50ml). Drying (MgSO4) followed by solvent removal yielded the product (V) (96g) as an off-white foam (97% yield).

Example 5. Deprotection of alkylated acetylated ioxithalamic acid amidated with trans-dioxepane to aminothreitol derivative 5-(N-2,3-Diacetoxypropylacetamido)-2,4,6-triiodo-N(2-acetoxyethyl)-N'-(trans-2,2-dimethyl-6-hydroxy-1,3-dioxepan-5-yl)-isophthalamide (V) into:
5-(N-2,3-Dihydroxypropylacetamido)-2,4,6-triiodo-N-(2-hydroxyethyl)-N'-(1,3,4-trihydroxy-threo-but-2-yl)-isophthalamide (VI)

The title compound (V) (4.94g, 5mMoles) was dissolved in methanol (20ml) and the pH was adjusted to 12–13 with 5N sodium hydroxide and the mixture agitated for 1hr at 25° C. to achieve complete deacetylation (by TLC). Upon evaporation to dryness, 15ml of 0.1N HCl was added (to pH 1–1.5), the solution stirred for 30min at 25° C. to obtain the product (by HPLC) which, after evaporation of acid and redissolving in water, was desalted with AG-501 mixed bed ion exchange resin. The solution was decolorized with charcoal and the solvent removed in vacuo to obtain the product (VI) as a white powder (3.2g) (78% yield).

Example 6. Amidation of alkylated, acetylated ioxithalamic acid with 1-amino-2,3-propanediol 5-(N-2,3-Dihydroxypropylacetamido)-2,4,6-triiodo-N-(2-hydroxyethyl)-N'-(1,3,4-trihydroxy-threo-but-2-yl)-isophthalamide (VI) into:

5-(N-2,3-Diacetoxypropylacetamido)-2,4,6-triiodo-N(2-acetoxyethyl)-N'-(2,3-dihydroxypropyl) isophthalamide (VII)

The title compound (VI) (86.25g, 100mMoles) was dissolved in dimethylacetamide (200ml) to which triethylamine (13.9g, 100mMoles) and 1-amino-2,3-propanediol (10.93g, 120mMoles) were added. The reaction was stirred at room temperature for 8hr to completion by TLC. The solvent was evaporated in vacuo and the product dissolved in tetrahydrofuran (75ml) and partitioned with water saturated with sodium chloride. The organic extract was washed with brine: 1N hydrochloric acid (9:1, 50ml×2), followed by brine:water (1:1) (50ml×2) and finally brine (40ml×1). The organic layer was dried over MgSO4 and the solvent was removed to give 80.6g of the product (VII) as an off-white foam (87.9% yield).

Example 7. Deprotection of alkylated, acetylated ioxithalamic acid amidated with 1-amino-2,3-propanediol 5-(N-2,3-Diacetoxypropylacetamido)-2,4,6-triiodo-N(2-acetoxyethyl)-N'-(2,3-dihydroxypropyl)isophthalamide (VII) into:

5-(N-2,3-Dihydroxypropylacetamido)-2,4,6-triiodo-N(2,3,-dihydroxypropyl)-N'-(2-hydroxyethyl)isophthalamide (VIII)

The title compound (VII) (9.17g, 10mMoles) was dissolved in methanol (20ml), the pH adjusted to 13 with 5N sodium hydroxide and stirred at room temperature for 30min to achieve complete deacetylation (by TLC and HPLC). The solution was neutralized with Dowex 50 H+resin, and evaporated to give 7.8g of an off-white foam (99% yield). This product was dissolved in water and decolorized with charcoal. Removal of the solvent gave the product (VIII) as a white foam (6.3g) (80% yield).

NMR: (1 H, 80 MHz, DMSO d6): 8.6 (2 H, broadened multiplet, carbamoyl N-H); 5.1–4.0 (5 H, broad singlet, exchangeable, hydroxyl protons); 4.1–2.8 (14 H, multiplet, protons-on-carbon bearing nitrogen and hydroxyl functions); 1.8 (3 H, singlet, acetanilide methyl protons).

TLC: silica gel 70:30 CHCl3MeOH: rf (acetylated compound VII) 0.84; rf (product compound VIII) 0.20.

HPLC: aminopropyl Alltech, 10μ, 3ml/min of 90% acetonitrile/water.

rf: 5.0 and 8.2 for two isomers.

Elemental Analysis: Calculated for $C_{18}H_{24}I_3N_3O_8H_2O$: C,26–71; H,3.26; I,47.05; N,5.19%; Found: C,26.45, H,3.30; I,46.71; N,4.80%.

Example 8. Amidation of alkylated, acetylated ioxithalamic acid chloride 5-(N-2,3-Diacetoxypropylacetamido)-2,4,6-triiodo-N(2-acetoxyethyl)-isophthalamic acid chloride (IV) into:

5-(N-2,3-Dihydroxypropylacetamido)-2,4,6-triiodo-N,N-bis-(2-hydroxyethyl)-N'-(2-hydroxyethyl)isophthalamide (IX)

The title compound (IV) (4.31g, 5mMoles) was dissolved in dimethylacetamide (10ml) and triethylamine (0.7ml, 5mMoles) and diethanolamine (0.79g, 7.5 mMoles) were added. The reaction mixture was at room temperature for 8hr to completion by TLC. Following evaporation of the solvent in vacuo, residue was partitioned between tetrahydrofuran (50ml) and brine (50ml). The organic layer was washed with brine: conc. HCl (9:1, 15ml×1), followed by 75% saturated brine (20ml×3). The organic extracts were dried over MgSO4 and the solvent removed to give 4.5g of an off-white foam (94% yield). The material was deprotected as described in Example 7, and desalted on mixed bed resin (AG-501) to yield 4.2g of final product (IX).

Example 9. Amidation of alkylated, acetylated ioxithalamic acid chloride with serinol 5-(N-2,3-Diacetoxypropylacetamido)-2,4,6-triiodo-N(2-acetoethyl)-isophthalamic acid chloride (IV) into:

5-(N-2,3-Dihydroxypropylacetamido)-2,4,6-triiodo-N-(1,3-dihydroxyisopropyl)-N'-(2-hydroxyethyl)isophthalamide (X)

To the solution of the title compound (IV) (12.3g, 14.3mMoles) in dimethylacetamide (54ml) was added triethylamine (2.0ml; 14.3mMoles) and serinol (1.56g, 17.2mMoles). The reaction mixture was stirred at room temperature for 8hr to completion by TLC. The solvent was removed in vacuo and to the residue tetrahydrofuran (20ml) and brine (20ml) were added. The aqueous layer was extracted with tetrahydrofuran (2×10ml). The organic layer was dried (MgSO4) and the removal of the solvent gave an off-white solid (11.45g), which was deacetylated as described in Example 7. Desalting of the crude product on Dowex mixed bed resin (AG-501), followed by decolorization with charcoal and evaporation, yielded the product (X) (10.1g) (77% yield).

Sodium isophthalamate (200g, 314mMoles) was dissolved in water (314ml) and the pH adjusted to 11. The solution was heated to 90° C and 1-chloro-2,3-propanediol (48.7g, 441mMoles) was added dropwise, while maintaining the pH at 11 by addition of 5M sodium hydroxide. The mixture was heated for 30min and then cooled to room temperature. The pH of the pale yellow solution was lowered to 5 by addition of concentrated hydrochloric acid. The solvent was removed in vacuo and the residue was dried by co-evaporation with pyridine (50ml). A white solid (307g) was obtained, which contained the expected product (XII), in addition to inorganic salt. This was acetylated as described in Example 11.

Example 10. Alkylation of sodium iothalamate

Sodium Iothalamate (XI)
5-Acetamido-2,4,6-triiodo-N-methylisophthalamic acid (XI) into:
5-(N-2,3-Dihydroxypropylacetamido)-2,4,6-triiodo-N-'-methylisophthalamic acid (XII)

Sodium iothalamate (XI) (146g, 229.5mMoles) was dissolved in lN sodium hydroxide (380ml), followed by addition (over 30min) of 1-chloro-2,3-propanediol (28.75ml; 344mMoles); pH was adjusted with 5N NaOH to 11.5–12.0. The mixture was brought to 85° C. and stirred for 2hr to completion by TLC. The pH was adjusted to 6–7 with concentrated hydrochloric acid and the water removed on an evaporator. The residue was azeotroped with toluene (100ml×1) to give 215g of an off-white product (XII) which without isolation was acetylated in the next reaction.

Example 11. Acetylation of the alkylated iothalamic acid 5-(N-2,3-Dihydroxypropylacetamido)-2,4,6-triiodo-N-methylisophthalamic acid (XII) into:
5-(N-2,3-Diacetoxypropylacetamido)-2,4,6-triiodo-N-methylisophthalamic acid (XIII)

To the crude product (XII) (307g) from Example 10 were added pyridine (25ml) followed by acetic anhydride (400ml), with cooling, such that the temperature was maintained below 50° C. The mixture was heated at 50° C. for 1hr and the solvents were removed in vacuo. The residue was co-evaporated with toluene (2×100ml) and dissolved in a mixture of ethyl acetate (300ml) and aqueous sodium bicarbonate (750ml). The aqueous layer was extracted with ethyl acetate (2×200ml) and acidified with concentrated hydrochloric acid to pH 0.5. The mixture was extracted with ethyl acetate (3×300m) and the combined organic layers were washed with water (2×100ml) and brine (2×50ml) and dried MgSO4) Removal of the solvent gave the product (XIII) a light yellow foam (225g) (92% yield from sodium isophthalamate).

Example 12. Acylchlorination of the alkylated, acetylated iothalamic acid 5-(N-2,3-Diacetoxypropylacetamido)-2,4,6-triiodo-N-methylisophthalamic acid (XIII) into:
5-(N-2,3-Diacetoxypropylacetamido)-2,4,6-triiodo-N-methylisophthalamic acid chloride (XIV)

The product (XIII) of Example 11 (225g, 0.29mole) was dissolved in thionyl chloride (540ml), stirred and refluxed for 1hr, when TLC showed that the reaction was over. Thionyl chloride was distilled off at 50–60° C. at 100 Torr and the residue dried by co-evaporation with ethyl acetate (2×100ml). The off-white foamy product was dissolved in ethyl acetate (700ml), washed with saturated aqueous sodium bicarbonate (4×200ml) and brine (2×250ml). The organic layer was dried (MgSO4) and the solvent removed to give the product (XIV) as an off-white foam (197g) representing 79.4% yield as calculated from the iothalamic acid.

Example 13. Amidation of the chloride of the alkylated, acetylated iothalamic acid with cis-dioxepane cl 5-(N-2,3-Diacetoxypropylacetamido)-2,4,6-triiodo-N-methylisophthalamic acid chloride (XIV) into:
5-(N-2,3-Diacetoxypropylacetamido)-2,4,6-triiodo-N-(cis-2,2-dimethyl-6-hydroxy-1,3-dioxepan-5-yl)-N'-methylisophthalamide (XV)

The title compound (XIV) (10g, 12.65mMoles) was dissolved in dimethylacetamide (25ml) to which triethylamine (1.8ml, 12.65mMoles) and cis-5-amino-2,2-dimethyl-6-hydroxy-1,3-dioxepane (2.44g, 15.2mMoles) were added. The solution was stirred at room temperature for 8hr, when the reaction was complete. The solvent was removed in vacuo and the residue dissolved in ethyl acetate (50ml). The solution was washed with water (3×25ml) and brine (2×25ml). Drying (MgSO4), followed by solvent removal, gave the product (XV) as an off-white foam.

Example 14. Deprotection of alkylated, acetylated iothalamic acid amidated with cis-dioxepane to D,L-aminoerythritol derivative 5-(N-2,3-Diacetoxypropylacetamido)-2,4,6-triiodo-N-(cis-2,2-dimethyl-6-hydroxy-1,3-dioxepan-5-yl)-N'-methylisophthalamide (XV) into:
5-(N-2,3-Dihydroxypropylacetamido)-2,4,6-triiodo-N-methyl-N'-(1,3,4-trihydroxy-erythro-but-2-yl) isophthalamide (XVI)

To a solution of the title compound (XV) (7.9g, 8.63mMoles) in methanol (30ml) was added 5N NaOH to pH 13. By TLC, deacetylation was complete after 30min at 24° C. The solution was treated with Dowex 50H+resin and the solvent removed on a rotary evaporator to give 6.78g foam (96% yield), which was dissolved in H2O (30ml). 1N HCl (3ml) was added and the mixture stirred for 1hr at 25° C. The solvents were removed on a rotary evaporator, and the residual acid removed with Dowex mixed-bed resin (AG-501). Charcoaling and evaporation gave 5.9g of product (XVI as a white foam (5.9g) (86% yield).

Example 15. Amidation of alkylated, acetylated iothalamic acid chloride with protected D,L-aminothreitol 5-(N-2,3-Diacetoxypropylacetamido)-2,4,6-triiodo-N-methylisophthalamic acid chloride (XIV) into:
5-(N-2,3-Diacetoxypropylacetamido)-2,4,6-triiodo-N-(trans-2,2-dimethyl-6-hydroxy-1,3-dioxepan-5-yl)-N'-methylisophthalamide (XVII)

To the solution of the title compound (XIV) (llg, 13.9mMoles) in dimethylacetamide (25ml) were added triethylamine (1.9ml; 13.9mMoles) and trans-5-amino-2,2-dimethyl-6-hydroxy-1,3-dioxepane (2.69g, 16.7mMoles). The reaction mixture was stirred at room temperature for 8hr to completion by TLC. The solvent was removed in vacuo and the residue dissolved in ethyl acetate (50ml). The solution was washed with water (3×25ml) and brine (2×25ml). Drying (MgSO4), followed by solvent removal, gave the product (XVII) as a pale yellow foam.

Example 16. Deprotection of alkylated, acetylated iothalamic acid amidated with trans-dioxepane to D,L-aminothreitol derivative 5-(N-2,3-Diacetoxypropylacetamido)-2,4,6-triiodo-N-(trans-2,2-dimethyl-6-hydroxy-1,3-dioxepan-5-yl)-N'-methylisophthalamide (XVII) into:
5-(N-2,3-Dihydroxypropylacetamido)-2,4,6-triiodo-N-methyl-N'-(1,3,4-trihydroxy-threo-but-2-yl)isophthalamide (XVIII)

To a solution of the title compound (XVII) (4.5g, 4.92mMoles) in methanol (15ml) was added 5N NaOH to pH 13. By TLC, deacetylation was complete after 30min at 24° C. The solution was treated with Dowex 50-H+resin and the solvent removed on a rotary evaporator to give 4.30g foam, which was dissolved in H$_2$O (30ml). 1N HCl (3ml) was added and the solution stirred for 1hr at 25° C. The solvents were removed on a rotary evaporator, and the residual acid removed with Dowex mixed-bed resin (AG-501). Charcoaling and evaporation gave the product (XVIII) as a white foam (3.6g) (93% yield).

Example 17. Alkylation of metrizoic acid with chloropropanediol

3-Acetamido-5-(N-methylacetamido)-2,4,6-triiodobenzoic acid (XIX) into:
3-(N-2,3-Dihydroxypropylacetamido)-5-(N-methylacetamido)-2,4,6-triiodobenzoic acid (XX)

The title compound (XIX) as the sodium salt (15g, 23.1mMoles) was dissolved in 100ml water to which 5N sodium hydroxide was added to pH 12-13. 1-Chloro-2,3-propanediol (2.81g, 25.4mMoles) was added dropwise over 15min, and the pH adjusted to 12-13 with additional 5N sodium hydroxide. After 1.5hr at 50-60° C., the reaction was indicated as completed by TLC; 2N HCl was added to pH 7 and the solvents removed in vacuo. The residue was dried by co-evaporation with pyridine. The resulting foamy product, weighing 26.1g and containing inorganic salt, was used directly in Example 18.

Example 18. Acetylation of N-alkylated metrizoic acid 3-(N-2,3-Dihydroxypropylacetamido)-5-(N-methylacetamido)-2,4,6-triiodobenzoic acid (XX) into:
3-(N-2,3-Diacetoxypropylacetamido)-5-(N-methylacetamido)-2,4,6-triiodobenzoic acid (XXI)

The crude product (26.1g) produced in Example 17 was suspended in acetic anhydride (26.2ml; 277mMoles) to which pyridine (25ml) was also added. Upon stirring, at 50° C., for 1hr, the reaction was complete by TLC. The solvents were removed in vacuo and the residue was co-evaporated with toluene (2×20ml) and dissolved in a mixture of ethyl acetate (100ml) and aqueous sodium bicarbonate (100ml). The aqueous layer was extracted with ethyl acetate (2×25ml) and acidified with concentrated hydrochloric acid to pH 0.5. The mixture was extracted with ethyl acetate containing 10% of tetrahydrofuran (3×50ml) and the combined organic layers were washed with water (2×25ml) and brine (2×25ml) and dried (MgSO$_4$). Removal of the solvent gave the product (XXI) as an off-white solid (17.5g) (96% yield based on metrizoic acid).

Example 19. Acylchlorination of acetylated, alkylated metrizoic acid 3-(N-2,3-Diacetoxypropylacetamido)-5-(N-methylacetamido)-2,4,6-triiodobenzoic acid (XXI) into:
3-(N-2,3-Diacetoxypropylacetamido)-5-(N-methylacetamido)-2,4,6-triiodobenzoyl chloride (XXII)

The title compound (XXI) (15g, 19.1mMoles) was suspended in thionyl chloride 40ml and heated to reflux with stirring. At 1hr, TLC indicated completion of the reaction. Thionyl chloride was distilled off in vacuo. Following dissolution in 40ml chloroform and extraction with 40ml saturated bicarbonate, washing with water and brine, the organic layer was dried over MgSO$_4$, filtered and solvents evaporated in a Rotovap to yield the product (XXII) (14.6g) (95% yield) as a yellow solid. MP 145-150° (dec).

Example 20. Amidation of metrizoic acid chloride (previously acetylated and alkylated) with trans-dioxepane 3-(N-2,3-Diacetoxypropylacetamido)-5-(N-methylacetamido)-2,4,6-triiodobenzoyl chloride (XXII) into:
3-(N-2,3-Diacetoxypropylacetamido)-5-(N-methylacetamido)-2,4,6-triiodo-N-(trans-2,2-dimethyl-6-hydroxy-1,3-dioxepan-5-yl)-benzamide (XXIII)

The title compound (XXII) (8g; 9.94mMoles) was dissolved in dimethylacetamide (20ml) and to this solution were added triethylamine (1.4ml; 9.96mMoles) and trans-5-amino-2,2-dimethyl-6-hydroxy-1,3-dioxepane (1.9g; 11.9mMoles). The reaction mixture was stirred at room temperature for 8hr, when the reaction was complete by TLC. The solvent was removed in vacuo and the residue dissolved in dichloromethane (40ml). The solution was washed with water (3×25ml) and brine (2×25ml). Drying (MgSO$_4$), followed by solvent removal, gave the product (XXIII) as a yellow foam (9.20g) (99% yield).

Example 21. Deprotection of alkylated metrizoic acid with trans-dioxepane to D,L-aminothreitol derivative 3-(N-2,3-Diacetoxypropylacetamido)-5-(N-methylacetamido)-2,4,6-triiodo-N-(trans-2,2-dimethyl-6-hydroxy-1,3-dioxepan-5-yl)-benzamide (XXIII) into:
3-(N-2,3-Dihydroxypropylacetamido)-5-(N-methylacetamido)-2,4,6-triiodo-N-(1,3,4-trihydroxy-threo-but-2-yl)-benzamide (XXIV)

The title compound (XXIII) (5g, 5.38mMoles) was dissolved in 23ml methanol and 2.7ml of 0.2M sodium hydroxide in methanol was added. After 1.5hr the solution was evaporated to dryness (4.3g, 94% yield), to which 13ml water and 0.025ml of concentrated HCl (0.3mMoles) was added. After 2hr of stirring the solution was neutralized with 1.26ml 1N sodium hydroxide and desalted on a mixed bed AG-501 ionic exchange resin to obtain athe product (XXIV) as an off-white solid (3.27g) (75% yield).

Example 22. Alkylation with subsequent acetylation of diatrizoic acid 3,5-Diacetamido-2,4,6-triiodobenzoic acid (diatrizoic acid) (XXV) into:
3,5-bis-(N-2,3-Diacetoxypropylacetamido)-2,4,6-triiodobenzoic acid (XXVI)

Diatrizoic acid (XXV) (205.6g; 0.32Mole) was dissolved in 6.45N aqueous sodium hydroxide (160ml).

The solution was heated to 45° C. and with mechanical stirring 1-chloro-2,3-propanediol (77.9g, 0.7Mole) was added dropwise during 15min. The reaction mixture was heated at 45° C. for 5hr and then neutralized to pH 7.0 by the addition of concentrated hydrochloric acid (2.4ml). The solvent was removed in vacuo at 50° C. and the residue was dried by azeotropic distillation with pyridine (3×150ml). To the resulting white foam (345g) were added pyridine (100ml; 1.27Moles) and acetic anhydride (260ml; 2.76Moles) with cooling to maintain the temperature at 40° C. The mixture was heated at 40° C. for 1hr, and then treated with water (100ml), with ice-cooling, for 30min. The solution was diluted with water (500ml) and extracted with a mixture of ethyl acetate/toluene (1:3) (4×200ml). The combined organic layers were washed with water containing 10% sodium chloride (5×300ml) and with brine (2×100ml). Drying (MgSO$_4$) followed by solvent removal yielded the product (XXVI) as a white foam (260g) (87% yield from diatrizoic acid).

The above procedures demonstrate the simple, rapid and efficient synthetic strategy of the subject invention. The high yields are evident and the use of intermediates without further purification further enhances the economics of the method. In addition, simple inexpensive reagents are employed at each stage, which can be readily removed, so as to leave the product substantially free of impurities. The number of steps from the starting material is limited to further minimize separations and purifications required by a large number of intermediates.

Compounds VIII and XVI were tested from stability, solubility, osmolality, viscosity and systemic toxicity. Using conventional tests, the subject compounds were compared with existing compounds and shown to have substantially reduced osmolality, while having comparable properties in the other categories.

TABLE

| | Properties of Preferred Novel Compounds and of the Prior Art Non-ionic CM* | | | | |
|---|---|---|---|---|---|
| | Compound VIII | Compound XVI | Iopromide | Iohexol | Iopamidol |
| Osmolality (mOsm/kg) | 560 | 513 | 607+ | 690+ | 619+ |
| Viscosity (cps) | 5.3 | 5.2 | 4.8+ | 6.1+ | 4.5+ |
| Estimated i.v. LD50(gI/kg)° Mice (CD-1) | 16–17 | 12–13 | 11.5–13.0 | 16–17 | 17–18 |
| Rats (Lewis) | 14–16.5 | 13.5–14 | 10–11.5 | 13.5–15 | 12.2–13 |

*All at 300 mg I/ml concentration and 37° C. Injection rates 1 ml/min in mice and 5 ml/min in rats.
+Ref. Handbook of Experimental Pharmacology, Vol. 73, M. Sovak, ed., Springer-Verlag 1984, Table 1, p. 9.
°Ref. Salvesen, S. in Acta Radiol. Suppl. 362, p. 73, 1980

It is evident from the above results, that the subject compounds provide improvement in contrast media, since hyperosomolality is related to vascular pain and solutions of osmolality reduced to the above range are known to be painless in clinical arteriography.

Although the foregoing invention has been described in some detail by way of illustration and example for purposes of clarity of understanding, it will be obvious that certain changes and modifications may be practiced within the scope of the appended claims.

What is claimed is:

1. In a method of X-raying a host employing a contrast medium, the improvement which comprises employing as a contrast medium 5-(N-2,3-dihydroxypropylacetamido)-2,4,6-triiodo-N-(2,3-dihydroxypropyl)-N'-(2-hydroxyethyl)-isophthalamide.

* * * * *